United States Patent
Kirchmayr et al.

(10) Patent No.: US 9,085,470 B2
(45) Date of Patent: Jul. 21, 2015

(54) SEPARATION METHOD

(75) Inventors: Roland Kirchmayr, Graz (AT);
Michael Harasek, Vienna (AT);
Christian Maier, Vienna (AT);
Reinhold Waltenberger, Linz (AT)

(73) Assignee: BDI—BIOENERGY INTERNATIONAL GMBH, Grambach/Graz (AT)

( * ) Notice: Subject to any disclaimer, the term of this patent is extended or adjusted under 35 U.S.C. 154(b) by 81 days.

(21) Appl. No.: 13/695,868

(22) PCT Filed: Feb. 25, 2011

(86) PCT No.: PCT/AT2011/000093
§ 371 (c)(1),
(2), (4) Date: Nov. 2, 2012

(87) PCT Pub. No.: WO2011/137466
PCT Pub. Date: Nov. 10, 2011

(65) Prior Publication Data
US 2013/0047852 A1    Feb. 28, 2013

(30) Foreign Application Priority Data
May 3, 2010    (AT) .................................. A 751/2010

(51) Int. Cl.
*B01D 19/00*    (2006.01)
*C02F 1/06*    (2006.01)
*C12M 1/107*    (2006.01)
*C12M 1/00*    (2006.01)
*C02F 1/04*    (2006.01)
*C02F 11/04*    (2006.01)
*C02F 101/16*    (2006.01)

(52) U.S. Cl.
CPC .................. *C02F 1/06* (2013.01); *C12M 21/04* (2013.01); *C12M 47/00* (2013.01); *C02F 1/048* (2013.01); *C02F 11/04* (2013.01); *C02F 2101/16* (2013.01); *Y02E 50/343* (2013.01)

(58) Field of Classification Search
CPC ......... B01D 19/0036; C02F 1/20; C02F 1/06; C02F 2101/16
USPC ....................... 95/266; 96/193, 201
See application file for complete search history.

(56) References Cited

U.S. PATENT DOCUMENTS

| | | | |
|---|---|---|---|
| 5,785,852 A | 7/1998 | Rivard et al. | |
| 7,781,194 B2 | 8/2010 | Weidele | |
| 2004/0025715 A1* | 2/2004 | Bonde et al. | 99/485 |
| 2006/0006055 A1* | 1/2006 | Bonde | 203/73 |

(Continued)

FOREIGN PATENT DOCUMENTS

| | | |
|---|---|---|
| CN | 100443137 C | 12/2008 |
| DE | 4341713 A1 | 6/1995 |

(Continued)

*Primary Examiner* — Duane Smith
*Assistant Examiner* — Adam W Bergfelder
(74) *Attorney, Agent, or Firm* — Fitzpatrick, Cella, Harper & Scinto

(57) ABSTRACT

The invention relates to a method for removing ammonia or reducing ammonium from biogas plant fermentation liquids or biogas plant fermentation residues, wherein ammonia or ammonium is reduced by way of flash evaporation, separated from the biogas plant fermentation liquids or biogas plant fermentation residues, and removed as ammonia. The invention further relates to a device for performing said method.

10 Claims, 2 Drawing Sheets

(56) References Cited

U.S. PATENT DOCUMENTS

| | | | |
|---|---|---|---|
| 2008/0302722 A1* | 12/2008 | Burke | 210/603 |
| 2009/0035834 A1 | 2/2009 | Weidele | |
| 2009/0050134 A1 | 2/2009 | Friend et al. | |
| 2010/0037772 A1* | 2/2010 | Roe et al. | 95/42 |
| 2014/0033776 A1* | 2/2014 | Josse et al. | 71/10 |

FOREIGN PATENT DOCUMENTS

| | | | |
|---|---|---|---|
| DE | 10063888 | A1 | 7/2002 |
| DE | 10353728 | A1 | 6/2005 |
| DE | 102005047719 | A1 | 4/2007 |
| JP | 2003039036 | A * | 2/2003 |
| JP | 2009018211 | A | 1/2009 |

* cited by examiner

SEPARATION METHOD

BACKGROUND OF THE INVENTION

1. Field of the Invention

The present invention relates to a method for removing ammonia or reducing ammonium, respectively, from fermentation liquids or fermentation residues used in the production of biogas.

2. Background of the Invention

The energy-related utilization of waste products and by-products has been gaining more importance in the sustainable production of consumer goods. In particular in the field of food production, any occurring organic waste may be used, by making use of the biogas technology, in order to (partially) cover the energy requirements of the production. In this way, the digestion of waste in the framework of production-integrated environmental protection and the production of renewable energy may contribute to the sustainable development of the company. On a national level, such measures are also desirable, as they contribute to the "2020 climate objectives" stipulated by the European Union.

The biogas that is formed by the residual substances accumulating in the production may be converted into electrical current and heat in a combined heat and power plant (BHKW). Alternatively, biogas could be processed, directly substituting fossil natural gas. By integration in an operation it may be guaranteed that the thermal energy is used all over the year, in this way guaranteeing the efficient use of the energy carrier with high overall efficiency. As a positive side effect, the energy-consuming disposal of these materials may be omitted due their high water content, and valuable nutrients like nitrogen, phosphorus and potassium may be returned to agricultural areas, together with the fermentation residues.

The internationally increasing demand for meat and meat products and the production associated therewith is responsible for the increased production of non-edible animal by-products. Offal as possible new substrates of industrial origin show a high potential for the production of methane and are in no way in competition with the food production sector. These and many more similar residual substances such as, e.g., waste from the pharmaceutical industry as well as blood processing (plasma waste), waste from the protein and meat processing industry and yeasts and slurries from the fermentation of ethanol, however, may be processed using prior art technology only under difficult conditions in anaerobic waste treatment plants.

In many regions the soils are supplied with high amounts of nitrogen due to intensive agriculture and animal breeding. Additional nutrient introduction may entail increased eutrophication of the waters and pollution of the groundwater. Methods for removing nitrogen from biogas fermentation residues would enable for the concentration of the developing ammonia into a transportable form, which may be transported off the region and thus reduce the impact on nature. In this way, the biogas production could be increasingly used in regions, where it is difficult to use due to lacking agricultural areas.

A major problem on the way to an overall implementation of the anaerobic technology in the energy-related digestion of, e.g., offal is the high nitrogen content thereof. The degradation products of the nitrogen compounds ammonia ($NH_3$) and ammonium ($NH_4^+$) that are contained in the substrate will lead to inhibition of the microbiology when exceeding certain concentrations. These toxic substances lead to a reduced degradation of the used waste substances and, as a consequence, to an unstable biogas process. This is why the nitrogen containing substrates were frequently transferred to external biogas plants for co-fermentation, whereby the possibility of integrating the waste heat of the combined heat and power plant in the production operation is omitted and the total efficiency of the slaughter house is reduced.

The process described in this patent document constitutes a key technology for the anaerobic digestion of nitrogen-rich waste and by-products. The removal of the nitrogen charge from the biogas process guarantees a stable and efficient process procedure.

In the context of renewable energy and environmental protection on the company level, biogas plays an important role. One example thereof is the slaughtering and meat processing industry. Non-edible animal by-products offer huge energetic potential in the anaerobic digestion. Making use of prior art techniques, such highly nitrogen-containing substrates may be digested only under difficult conditions in biogas plants.

In the anaerobic fermentation, the used organic substances (such as, e.g., proteins, nucleic acids, fats and carbon hydrates) are incrementally degraded in the absence of oxygen by different anaerobic microorganisms into smaller compounds. Final products of the biogas process are methane ($CH_4$), carbon dioxide ($CO_2$) as well as not further degradable carbon and mineral compounds. The nitrogen bound in the biomass is released as ammonium ($NH_4^+$) and remains in the final fermentation product. Too high concentrations may inhibit the microbial process or even have toxic effects on the microorganisms. Independent of temperature and pH, ammonium is in equilibrium with ammonia ($NH_3$), which is considered as cytotoxin and has an inhibitory effect already at small concentrations.

In order to enable for raw materials having high nitrogen concentrations (e.g., protein-rich by-products of slaughter houses, waste from the leather industry, residual substances of the bio fuel production, etc.) being processed in anaerobic fermentation processes, the development of new strategies is necessary.

For the microbiology in the fermenter it is important that certain amounts of nitrogen components are available. These are required for the growth of the biomass; the amount absorbed by the microorganisms, however, only constitutes a fraction of the nitrogen amount contained in the present substrate. In the course of the biogas process illustrated in FIG. 1, in the absence of dissolved oxygen, polymer compounds are hydrolyzed by different heterotrophic anaerobic microorganisms.

The nitrogen containing polymers, proteins and nucleic acids are degraded in the first step into amino acids, purines and pyrimidines. In the further course of the biological degradation process, nitrogen is released in the form of ammonium and remains—in contrast to the biologically available organic substances that are converted into biogas—in the fermentation liquid. In this way, the nitrogen degradation products are even concentrated. With increasing pH and increased temperatures in the process, the reaction equilibrium shifts from ammonium towards ammonia.

Ammonia has toxic effects on bacteria, as nearly all biological membranes are permeable to ammonia due to the small size of the $NH_3$ molecule as well as the lipid solubility thereof.

Among the different microorganisms that are involved in the anaerobic digestion, the methanogenes are the ones being the least tolerant in regard to high concentrations of ammonium and, hence, most likely prone to inhibition and toxic effects. As a consequence of inhibition, this leads to small biogas yields and the accumulation of intermediate degradation products such as free volatile fatty acids. Apart from the reduced yields of renewable energy, the biological process hindrances further led to increased emissions of smell out of the final fermentation product due to insufficiently degraded substrates.

In order to solve the problem of nitrogen, there have so far been discussed in principle several approaches:
- Exclusion of specific substrates having high nitrogen content,
- Dilution of the nitrogen-rich substrate or
- Separation of the nitrogen from the substrate.

Though the exclusion and the dilution of specific substrates may be taken into consideration for individual plant operators, this way is, however, not successful as a solution to the present problem of the digestion of nitrogen-rich waste and by-products. Diluting the substrate, for example, with waste waters having low nitrogen concentrations, leads to an enormous demand of additional digestion space. At the same time, the efforts for the storage and the transport costs of the fermentation residues would be multiplied. The most successful approach, hence, is the discharge of the nitrogen component from the biogas process.

This procedure reduces the inhibition of the microorganisms by increased $NH_4^+/NH_3$ concentrations and, hence, exerts the following positive influences on the biogas process:
- Increased methane yields at stable fermenter volume
- Higher degradation rates enable for higher space load
- More stable biological process by preventing the accumulation of free volatile fatty acids (FFS), which also impede the efficiency of the process
- Reduction of undesired emissions of smell due to complete degradation of the organic mass By way of separation of significant amounts of the ammonium nitrogen, there may be guaranteed in an existing biogas plant an improved and more stable operation, and the degradation performance and, consequently, the methane yield are remarkably increased. In this way, it is possible to increase the space load of the fermenters, which is why in the future the entire substrate spectrum as well as the maximum gas yield thereof may be used for the production of energy.

Resulting from this significant increase in the performance, there are provided correspondingly higher yields of $CO_2$—neutral electricity and heat from the increased utilization of the combined thermal and power plants (BHKW). For the selected removal of ammonia from liquid media, there have already been developed a series of methods, in particular in the waste water technology. Some of these have been tested on a large-scale basis in part for a considerable period of time, thus being state of the art. For the relatively new sector of biogas, these technologies have been adapted and may be used in the field of fermentation residues processing. These technologies, however, are used only in exceptional cases due to the high efforts in terms of energy, operating materials and substrate pre-treatment.

In general, the procedures for removing nitrogen may be distinguished in biological and physical-chemical methods:

The nitrification/denitrification as a biological method represent an established technology of the biological waste water treatment. The removal of nitrogen, herein, is carried out in two partial steps:

1. Nitrification

The reaction of ammonium into nitrate under aerobic conditions is carried out by chemolithotrophic nitrifying bacteria. This oxidation is realized in two steps. Bacteria of the "nitroso group" are able to oxidize ammonia or ammonium up to the nitrite ($NO_2-$) (ammonium oxidizing agents). The further oxidation into nitrate ($NO_3-$) is performed by nitrobacteria types or other representatives of the "nitro group" (nitro oxidizing agents).

2. Denitrification

In the absence of oxygen, various aerobic waste water bacteria may oxidize organic compounds having nitrate instead of $O_2$. In the denitrification process, there are developed gaseous final products from the nitrate, this is mainly molecular nitrogen ($N_2$). As a by-product there may also be released nitrous oxide (laughing gas, $N_2O$).

As the first of the two reaction steps has to be performed in an aerobic atmosphere, this method that has often been tested in the waste water technology is unsuitable for the present case of the anaerobic biogas production, because in the aerobic step, the major part of the chemical energy would be used instead of being reacted into biogas.

The Anammox process (anaerobic ammonium oxidation) offers an alternative to the classic method of nitrification/denitrification. Therein, ammonium is reacted with nitrite under anaerobic conditions into molecular nitrogen. In spite of a plurality of descriptions in the literature, this process cannot be designated as prior art yet.

In regard to the biological methods, the advantage of the majority of physical-chemical methods is essentially that present ammonium nitrogen is not reacted into elementary nitrogen. The nitrogen thus is not released into the atmosphere but is rather available in different chemical compounds as a resource, depending on the method.

The removal of the dissolved nitrogen compounds from the fermentation medium may be carried out using so-called stripping methods. In general, stripping is the removal of volatile compounds from liquids using gas. By decreasing the partial pressure of the more volatile component, this transits from the dissolved state into the gaseous state in the gas phase and enriches in the liquid. The basic principle is represented as a unit having two main methodological steps:
- Ammonia elimination from the substrate using stripping gas (air or vapour, respectively)
- Regeneration of the stripping gas and transferral of the ammonium into a recyclable material flow In order to transfer the dissolved ammonia into the gaseous phase (desorption), there have been proven successful on a large-scale industrial basis methods of air and vapour stripping in filling body columns. The main characteristic thereof is that the liquid to be treated is brought into as intensive contact as possible with the gas flow. Therefore, a rather big mutual exchange area is of great importance. This is achieved by introducing filling bodies, at the surface of which the liquid phase will move along in the form of a film.

For the flawless operation of a stripping facility, the nearly complete removal of solids is a prerequisite, as otherwise this will lead to blocking/obstructing of the filling body coating. The level of the necessary removal of solids respectively depends on the type of filling bodies and the other facility structure.

With the aid of ion exchange methods, charged ingredients (ions, e.g., ammonium $NH_4^+$) may be adsorbtively bound and exchanged for ions having the same charge. There are predominantly used synthetic resins, so-called ion exchange resins. A rather comprehensive pre-treatment of the substrate, in particular the removal of solids, is a necessary prerequisite. Because of the structure of the ion exchange material, this is relatively sensitive in regard to the obstruction of the hollow spaces, for example, by organic colloids, whereby the performance is largely reduced. Thus the use is only profitable, according to the present state of the art, for post-treatment, e.g. following already performed nanofiltration or return osmosis in order to securely guarantee the given limit values, which is why it is unsuitable for the treatment of the fermentation medium that is aimed for.

A variant of the ammonium extraction recently examined is the use of extractive membranes in membrane contactors. Membrane contactors with pervaporation are novel apparatuses for performing extraction or stripping processes, respectively, in which the phase exchange takes place at a membrane surface. In conventional stripping columns the liquid and the gaseous phase are in direct contact, wherein the necessary intensive mixing is obtained by sprinkling with filling bodies. In membrane contactors, the two phases are present separated from each other by a membrane that is only permeable to gaseous ammonia.

In the connection with membrane reactors, however, there is existent a series of unanswered questions, such as, e.g., the long-term stability and proneness to fouling of the membranes. In total, these methods are still in an early phase of development, and presently it is still unclear whether realization and real implementation will be successful.

SUMMARY OF THE INVENTION

It is the task of the present invention to overcome the disadvantages of the above mentioned prior art methods and to provide a method for removing ammonia or reducing ammonium, respectively, from slaughter house waste waters used for the production of biogas as well as a device for performing this method. This task is solved according to the invention in that in a method of the above mentioned type ammonia or ammonium, respectively, is removed by way of flash evaporation, separated from the slaughter house waste waters and removed as ammonia. Therein, a part of the water content of the fermentation liquid that is circulated is evaporated by overheating and subsequent atomization in a vessel under vacuum. In this way, a portion of the nitrogen may be separated as ammonia and subsequently collected as recyclable material. The developed process for the removal of nitrogen from slaughter house waste waters used for the production of biogas is based on the principle of flash evaporation. In this method, the liquid to be treated is sprayed, following coarse contamination separation (e.g., screw press, vibrating screen) and heating via a nozzle, in a vessel under sub pressure. Exceeding the boiling point associated with the pressure reduction leads to spontaneous evaporation (flash) at the surface of every individual one of the fine droplets. This evaporation is the driving force in the removal of volatile substance such as, e.g., ammonia. The loaded vapour (exhaust vapour) is discharged and condensed. In the sump of the container, the liquid having a reduced volume is withdrawn and possibly supplied following further heating in the circle to a further expansion and, hence, evaporation step. This technology was originally developed for the desalination of sea water; the treatment of media from biogas fermenters, hence, constitutes a novel area of application for such flash evaporators.

BRIEF DESCRIPTION OF THE DRAWINGS

For a better understanding of the present invention, reference is made to the following drawings. Referring to the Drawings.

DETAILED DESCRIPTION OF THE INVENTION

Figure 1:
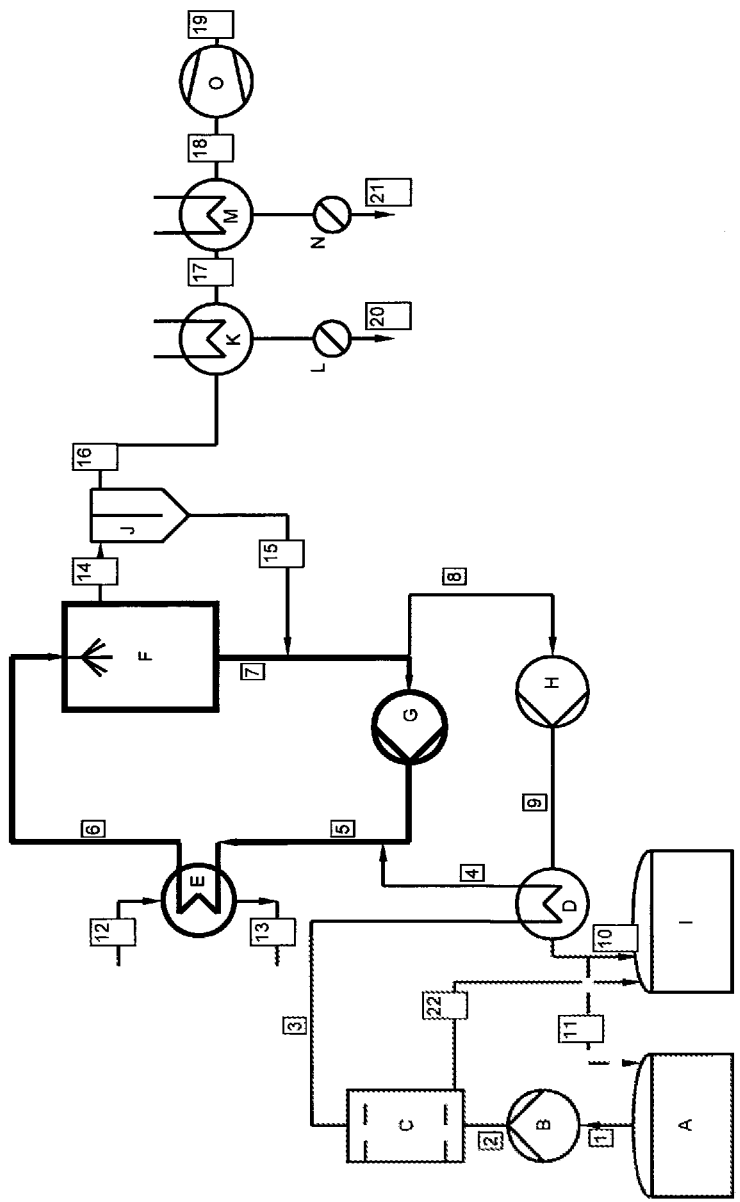
FIG. 1 shows an exemplary embodiment of a method for removing ammonia or reducing ammonium, respectively, from fermentation liquids or fermentation residues in the production of biogas.

Preferably up to 50%, especially preferably up to 30% of the entire nitrogen of the biogas plant fermentation liquids or biogas plant fermentation residues is separated. By way of this removal, there may be guaranteed an uninhibited biogas process. In this way, in the future all flows that accumulate, e.g., in a slaughter house or any other facility and that are suitable for the anaerobic digestion may be energetically utilized with simultaneously improved levels of degradation. This will lead to an increase in the production of renewable energies, which will be able to cover up to 75% of the energy consumption of the industrial plant. In substrates having a very high nitrogen content it is useful to arrange the removal of ammonia already upstream of the anaerobic digestion or to have this integrated therein in order to maximize the biogas yield.

It is especially favourable if the biogas plant fermentation liquids or biogas plant fermentation residues are already pre-heated by the residual heat of the already treated medium before the flash evaporation. In the process (see FIG. 2), the material is directly taken from the biogas fermenter or the fermentation residue storage. The medium is pre-heated in a counter-flow heat exchanger by means of 80° hot discharge of the plant to about 70° C. and then introduced in an internal recirculation circuit. The internal recirculation represents a set point for the desired distance rates, as this is, among others, dependent on the evaporation rate, which may be adjusted by the recirculation rate. In a second heat exchanger, the medium is heated to the required entry temperature of the flash evaporator of about 90° C. When entering the flash evaporator, the negative pressure prevailing there will immediately result in the evaporation of water, wherein also a portion of the ammonia is transferred into the gaseous phase. The exhaust vapours loaded with ammonia from the flash evaporator are condensed, and an aqueous ammonia solution is collected as product. From the recirculation flow, a continuously treated medium is removed from the flash reactor, is then cooled in the counter-flow heat exchanger by fresh resources and is then returned into the biogas plant.

The necessary evaporation energy is provided by a gas boiler. In the course of another energy-related optimization, a part of this energy may be substituted for heat (waste heat) developing at the site. Also the waste heat that is released in the condensation of the exhaust vapour may be integrated in the heat supply of the plant and of the operation.

The aqueous ammonia solution may, on the one side, be used as a valuable fertilizer in the local agriculture, or it may, on the other side, be used as a chemical basic substance, for example, in the purification of flue gases emitted by plants, for the denitrification.

According to another embodiment of the present invention, this relates to a device for separating ammonia or reducing ammonium, respectively, from biogas plant fermentation liquids or biogas plant fermentation residues, wherein a flash evaporator F is connected with a fermenter A via lines 1, 2, 3, 4, 5, 6 for supplying substrate, wherein exhaust vapour is withdrawn from the flash evaporator F via a line 14 and the hot liquid phase is returned either via line 11 into the fermenter A or supplied via line 10 into a second fermenter I.

In this connection it is favourable if there is provided in the line 2, 3 from the fermenter A an impurity separation C, which is connected via lines with a heat exchanger D for the liquid portions of the substrate, on the one side, and via line 22 with a second fermenter I for the solid portions of the substrate, on the other side.

Preferably in an inventive device the heat exchanger D is heated via line 9 with hot liquid phase from the flash evaporator F.

According to a preferred embodiment the pre-heated liquid phase is introduced from the heat exchanger D via line 4 in a circuit, comprising line 5, heat exchanger E, line 6, flash evaporator F, line 7 and pump G.

According to another embodiment there is provided that the hot liquid phase is supplied via a line 10 to a mixing tank P, which in turn is connected via lines with the fermenters A and I.

The present invention is now explained in greater detail by way of the accompanying drawings, to which, however, it shall not be limited.

Figure 2:
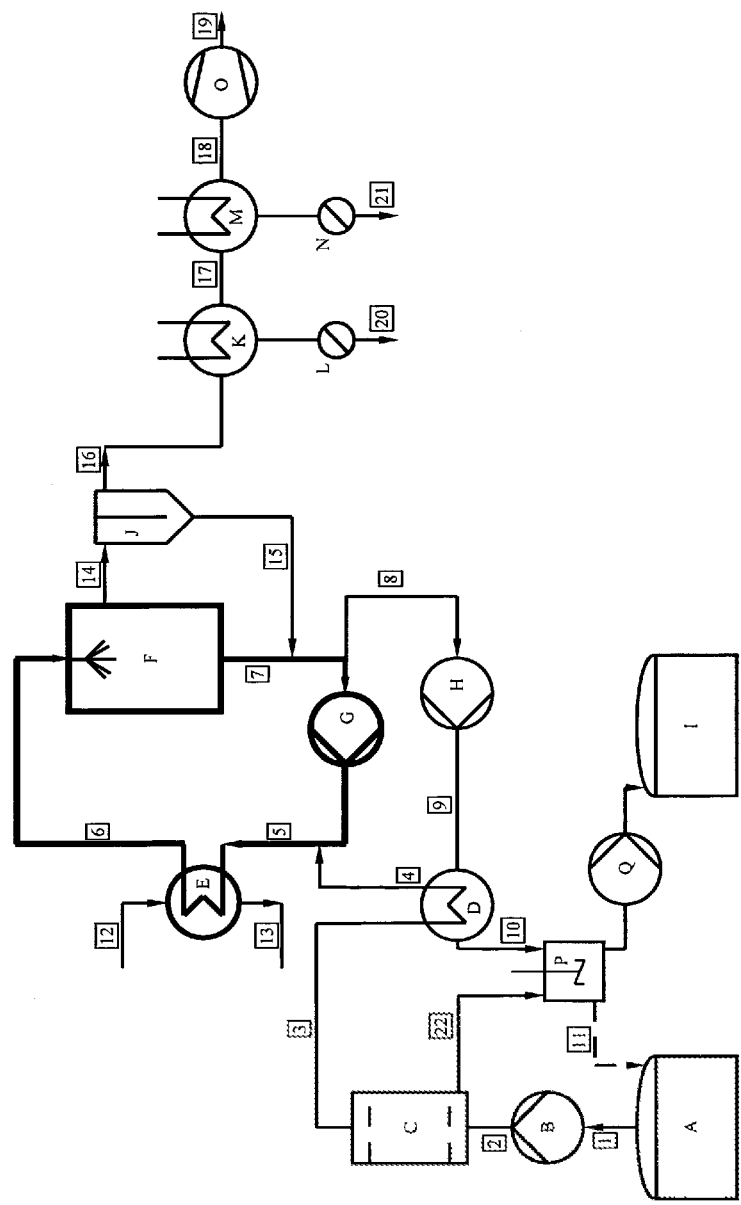
FIG. 2 shows another exemplary embodiment of a method for removing ammonia or reducing ammonium, respectively, from fermentation liquids or fermentation residues in the production of biogas.

In the FIGS. 1 and 2 there is shown one respective possible embodiment of the present invention, wherein:

A fermenter 1
B raw substrate pump
C impurity separation (vibrating screen, screw press)
D heat exchanger pre-heating
E heat exchanger
F flash evaporator
G circuit pump
H withdrawal pump
I fermenter 2
J droplet separation (e.g., cyclone)
K condensator, step 1
L condensate pump 1
M condensator, step 2
N condensate pump 2
O inert gas feed device
P mixing tank: resuspension of the separated solids
Q substrate pump
1 line for raw substrate flow
2 line for raw substrate flow
3 line for substrate, freed of solid impurities
4 line for pre-heated substrate
5 line for substrate in the circuit of the flash evaporator
6 line for substrate in the circuit of the flash evaporator, pre-heated for evaporation step
7 line for outflow from the flash evaporator (liquid phase)
8 line for withdrawal of $NH_3$ depleted substrate (discharge out of the circuit flow)
9 line for substrate flow
10 line for cooled and NH3-depleted substrate, introduction in fermenter
11 line for cooled and $NH_3$-depleted substrate, optional re-introduction in evacuation fermenter
12 line for heating medium inflow
13 line for heating medium outflow
14 line for exhaust vapour from the flash evaporator
15 line for droplets separated from the exhaust vapour
16 line for exhaust vapour flow
17 line for residual exhaust vapour, after the first condensator step
18 line for inert gases, after the second condensator step
19 line for inert gases to the gas treatment (e.g., bio filter)
20 line for condensate flow of the first condensator step
21 line for condensate flow of the second condensator step, $NH_3$-enriched
22 line for the solid portion separated from the raw substrate According to FIG. 1 the raw substrate to be treated is directly withdrawn from the biogas fermenter or fermentation residues storage A by means of the pump B. Solid substances that are contained in the medium are separated in the impurity separation C (e.g., screw press, vibration screen) from the liquid and are then introduced in the fermenter I. The liquid portion of the substrate (line 3) is pre-heated in the counter-flow with completely treated substrate from line 9 in the heat exchanger D (e.g., spiral heat exchanger) to a temperature of about 65 to 75° C. and then introduced via line 5 into the internal circuit. In a second heat exchanger E (e.g., condensator, fresh vapour from line 12) the medium is then heated to the entry temperature of about 80 to 95° C. that is necessary for the evaporation process.

When the medium is sprayed in the flash evaporator, the pre-pressure in line 6 is lowered from about 1.5 to 3.0 bara by way of the pressure loss of the spray nozzle to the operational pressure in the flash evaporator of about 500 to 700 mbar. Upon entry into the flash evaporator, the temperature will immediately fall below the boiling point due to the negative pressure prevailing there and, thence, to a spontaneous evaporation at the surface of the droplets of the atomized spray. This evaporation is the driving force in the removal of volatile substances such as, e.g., ammonia and dissolved carbon dioxide. Also a portion of the water in the substrate is evaporated in this step. The exhaust vapours loaded with $NH_3$ and $CO_2$ are supplied via line 14 to a droplet separation J (e.g., cyclone). Liquid that has been separated from the gas flow is re-supplied via line 15 to the liquid phase that has been withdrawn from the evaporator step in line 7. The circuit of the lines 5, 6, 7 is maintained by the pump G. The return rate as the ratio of circuit flow to fresh substrate may be adjusted by way of the pump performance of G, thus serving as a regulatory variable for the rate of $NH_3$ removal.

Treated substrate is continuously withdrawn from the circuit flow (line 8). This substrate that is $NH_3$- and $CO_2$-depleted is formed at a temperature of about 75 to 90 C. Before being pumped (pump H) into the fermenter I, the heat content of the flow of line 9 is cooled to about 40 to 55° C. by way of the counter-flow heat exchanger D (e.g., spiral heat exchanger), and in return the raw substrate is heated. The heating performance to be used may be massively reduced by this energy integration; the medium may further be introduced in the fermenter, without endangering the gas forming microbiology through supertemperatures. The cooled and treated substrate is then transported either via line 10 into the fermenter I or, if desired alternatively or additionally, via line 11 into the fermenter or the fermentation residues storage A.

The exhaust vapours loaded with $NH_3$ from the flash evaporator 14 are supplied to an exhaust vapour condensation. Following cooling to about 50 to 60° C. in the condensator K an aqueous ammonia solution 21 of 20 to 80 g/kg $NH_3$ may be supplied to the further material digestion (e.g., production of fertilizers, use as SNCR reagent in power plant technology, etc.).

In the shown embodiment the exhaust vapour condensation is configured in two phases. In the first condensate step K, the exhaust vapours are cooled to about 75 to 85° C. The first condensate is developed having a lower concentration of about 5 to 10 g/kg $NH_3$ (flow 20). Following further cooling to about 50 to 60° C. in the condensator M, an aqueous ammonia solution 21 having a higher ammonia concentration of 40 to 80 g/kg $NH_3$ may be supplied to further material digestion (e.g., production of fertilizers, use as SNCR reagent in the power plant technology, etc.,). Alternatively (not shown) also a single-step exhaust vapour condensation is possible.

The gases that cannot be condensed at the temperatures indicated for the condensation steps are sucked off via line 18 through an inert gas feed device O, which also maintains the system pressure of 500 to 700 bar in the flash evaporator.

In a particular embodiment this inert gas feed device O is configured for suction of the non-condensable gases as a water jet pump having water as circulating medium. This has the advantage that the sucked and not-condensable gases are simultaneously washed with the water jet pump water and are, hence, freed of any remaining traces of $NH_3$.

According to FIG. 2 the cooled and treated substrate is moved into a mixing tank P, where it is mixed with the solid particles from the impurity separation C (e.g., screw press, vibrating screen), whereupon the medium is transported either via line 11 in the fermenter A or, if desired alternatively or additionally, via line 10 and by means of the substrate pump Q in the fermenter I.

What is claimed is:

1. A method for removing ammonia or reducing ammonium, respectively, from biogas plant fermentation liquids or fermentation residues, which are produced in the fermentation of offal, wherein ammonia or ammonium, respectively, is reduced by way of flash evaporation, separated from the biogas plant fermentation liquids or biogas plant fermentation residues, and removed as ammonia, and wherein the biogas plant fermentation liquid or fermentation residue is sprayed at an entry temperature of 80° C. to 95° C. into an flash evaporator (F) via a spray nozzle, whereby a pre-pressure of the biogas plant fermentation liquids or fermentation residues before flash evaporation is lowered from 1.5 bar to 3.0 bar by way of pressure loss of the spray nozzle to an operational pressure in the flash evaporator (F) of 500 mbar to 700 mbar.

2. A method according to claim 1, wherein up to 50% of the total nitrogen of the biogas plant fermentation liquids or biogas plant fermentation residues are separated.

3. A method according to claim 1, wherein up to 30% of the total nitrogen of the biogas plant fermentation liquids or biogas plant fermentation residues are separated.

4. A method according to claim 1, wherein the removal of the ammonia is upstream of an anaerobic digestion.

5. A method according to claim 1, 2, 3 or 4, wherein the biogas plant fermentation liquids or biogas plant fermentation residues are pre-heated by a residual heat of an already treated medium before flash evaporation.

6. A device for separating ammonia or reducing ammonium, respectively, from biogas plant fermentation liquids or biogas plant fermentation residues, wherein a flash evaporator (F) is connected with a fermenter (A) or a fermentation residue storage via lines (1, 2, 3, 4, 5, 6) for supplying a substrate, wherein exhaust vapour is withdrawn from the flash evaporator (F) via a line (14) and a hot liquid phase is returned either via line (11) into the fermenter (A) or the fermentation residue storage or via line (10) into a second fermenter (I), fermentation residue storage or a further container, and wherein there is provided in the line (2, 3) from the fermenter (A) an impurity separation (C), which is connected via lines with a heat exchanger (D) for the liquid portions of the substrate, on the one side, and via line (22) with the second fermenter (I) for the solid portions of the substrate, on the other side.

7. A device according to claim 6, wherein the heat exchanger (D) is heated via line (9) with hot liquid phase from the flash evaporator (F).

8. A device according to claim 6 or 7, wherein a pre-heated liquid phase is introduced from a heat exchanger (D) via line (4) in a circuit, comprising line (5), heat exchanger (E), line (6), flash evaporator (F), line (7) and pump (G).

9. A device according to claim 6 or 7, wherein the hot liquid phase is supplied via a line (10) to a mixing tank (P), which in turn is connected via lines with the fermenters (A and I).

10. A device according to claim 8, wherein the hot liquid phase is supplied via a line (10) to a mixing tank (P), which in turn is connected via lines with the fermenters (A and I).

* * * * *